(12) United States Patent
Onishi et al.

(10) Patent No.: US 8,859,248 B2
(45) Date of Patent: Oct. 14, 2014

(54) METHOD FOR PRODUCING ETHANOL USING RECOMBINANT YEAST STRAIN

(75) Inventors: Toru Onishi, Toyota (JP); Emiko Tominaga, Chiryu (JP); Noriko Yasutani, Nagoya (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 13/883,670

(22) PCT Filed: Nov. 11, 2010

(86) PCT No.: PCT/JP2010/070076
§ 371 (c)(1),
(2), (4) Date: May 6, 2013

(87) PCT Pub. No.: WO2012/063344
PCT Pub. Date: May 18, 2012

(65) Prior Publication Data
US 2013/0224815 A1 Aug. 29, 2013

(51) Int. Cl.
*C12P 7/06* (2006.01)
*C12N 15/81* (2006.01)

(52) U.S. Cl.
CPC .. *C12P 7/06* (2013.01); *Y02E 50/16* (2013.01); *C12N 15/81* (2013.01); *Y02E 50/17* (2013.01)
USPC ................... 435/161; 435/254.2; 435/254.21; 435/254.22; 435/254.23

(58) Field of Classification Search
None
See application file for complete search history.

(56) References Cited

U.S. PATENT DOCUMENTS

| | | | |
|---|---|---|---|
| 6,582,944 B1 * | 6/2003 | Hallborn et al. | 435/161 |
| 2005/0153411 A1 * | 7/2005 | Wahlbom et al. | 435/161 |
| 2006/0234364 A1 * | 10/2006 | Rajgarhia et al. | 435/161 |
| 2007/0190629 A1 * | 8/2007 | Wahlbom et al. | 435/161 |
| 2008/0014620 A1 * | 1/2008 | Op Den Camp et al. | 435/161 |
| 2010/0112658 A1 * | 5/2010 | Hughes et al. | 435/161 |
| 2011/0027847 A1 * | 2/2011 | Matsushika et al. | 435/161 |
| 2011/0143409 A1 * | 6/2011 | Seo et al. | 435/161 |
| 2011/0262983 A1 * | 10/2011 | Jeffries et al. | 435/161 |
| 2011/0294170 A1 * | 12/2011 | Subbian et al. | 435/106 |
| 2012/0107889 A1 * | 5/2012 | Doty et al. | 435/158 |

FOREIGN PATENT DOCUMENTS

| | | |
|---|---|---|
| JP | 2009-195220 A | 9/2009 |
| JP | 2010-239925 A | 10/2010 |
| WO | WO 2004085627 A1 * | 10/2004 |
| WO | WO 2009109630 A1 * | 9/2009 |

OTHER PUBLICATIONS

Kastner et al., "Effect of pH on cell viability and product yields in D-xylose fermentations by *Candida shehatae*", Applied Microbiology and Biotechnology, vol. 45, pp. 224-228, 1996.*

Kruse et al., "Investigation of ethanol formation by *Pachysolen tannophilus* from xylose and glucose/xylose co-substrates", Process Biochemistry, vol. 31, No. 4, pp. 389-407, 1996.*

(Continued)

*Primary Examiner* — Rebecca Prouty
*Assistant Examiner* — Richard Ekstrom
(74) *Attorney, Agent, or Firm* — Sughrue Mion, PLLC

(57) ABSTRACT

This invention provides a method for improving the xylose-metabolizing ability of a yeast strain having xylose-metabolizing ability. The method comprises steps of: soaking the yeast strain having xylose-metabolizing ability in an acetic-acid-containing solution; and then, culturing the yeast strain in a xylose-containing medium to perform ethanol fermentation.

3 Claims, 3 Drawing Sheets

(56) References Cited

OTHER PUBLICATIONS

Toivari et al., "Conversion of xylose to ethanol by recombinant *Saccharomyces cerevisiae*: importance of xylulokinase (XKS1) and oxygen availability", Metabolic Engineering, vol. 3, pp. 236-249, 2001.*

Hou et al., "Impact of overexpressing NADH kinase on glucose and xylose metabolism in recombinant xylose-utilizing *Saccharomyces cerevisiae*", Applied Microbiology and Biotechnology, vol. 82, pp. 909-919, 2009.*

Eleonora Bellissimi, et al., "Effects of acetic acid on the kinetics of xylose fermentation by an engineered, xylose-isomerase-based *Saccharomyces cerevisiae* strain", FEMS Yeast Res., 2009, pp. 358-364, vol. 9.

Ana Maria Souto-Maior, et al., "Crabtree-negative characteristics of recombinant xylose-utilizing *Saccharomyces cerevisiae*", Journal of Biotechnology, 2009, pp. 119-123, vol. 143.

K. L. Traff-Bjerre, et al., "Endogenous NADPH-dependent aldose reductase activity influences product formation during xylose consumption in recombinant *Saccharomyces cerevisiae*", Yeast, 2004, pp. 141-150, vol. 21.

Stev Helle, et al., "Effect of inhibitory compounds found in biomass hydrolysates on growth and xylose fermentation by a genetically engineered strain of *S. cerevisiae*", Enzyme and Microbial Technology, 2003, pp. 786-792, vol. 33.

Akinori Matsushika, et al., "Ethanol production from xylose in engineered *Saccharomyces cerevisiae* strains: current state and perspectives", Appl. Microbol. Biotechnol., 2009, pp. 37-53, vol. 84.

Casey, et al., "Effect of acetic acid and pH on the cofermentation of glucose and xylose to ethanol by a genetically engineered strain of *Saccharomyces cerevisiae*", Federation of European Microbiological Societies, Apr. 14, 2010, p. 385-393.

* cited by examiner

METHOD FOR PRODUCING ETHANOL USING RECOMBINANT YEAST STRAIN

CROSS REFERENCE TO RELATED APPLICATIONS

This application is a National Stage of International Application No. PCT/JP2010/070076 filed Nov. 11, 2010, the contents of all of which are incorporated herein by reference in their entirety.

TECHNICAL FIELD

The present invention relates to a method for producing ethanol using a recombinant yeast strain having xylose-metabolizing ability.

BACKGROUND ART

A cellulose-based biomass is an effective starting material for a useful alcohol, such as ethanol, or an organic acid. In order to increase the amount of ethanol produced with the use of a cellulose-based biomass, yeast strains capable of utilizing an xylose, which is a pentose, as a substrate have been developed. For example, JP Patent Publication (Kokai) No. 2009-195220 A discloses a recombinant yeast strain resulting from incorporation of the xylose reductase gene and the xylitol dehydrogenase gene derived from *Pichia stipitis* and the xylulokinase gene derived from *S. cerevisiae* into its chromosome.

FEMS Yeast Research, vol. 9, 2009, 358-364 and Enzyme and Microbial Technology 33, 2003, 786-792 describe that culture of yeast strains provided with the xylose-metabolizing ability in a fermentation medium containing acetic acid results in lowered rates of xylose fermentation. In addition, Appl. Microbiol. Biotechnol., 2009, 84: 37-53 describes a yeast strain with the xylose-fermenting ability and a variant with an improved rate of xylose fermentation.

However, no techniques for improving the xylose-metabolizing ability of a yeast strain having such ability have been known.

SUMMARY OF THE INVENTION

Object to be Attained by the Invention

Under the above circumstances, it is an object of the present invention to provide a technique for improving the xylose-metabolizing ability of, in particular, a yeast strain having xylose-metabolizing ability to improve ethanol productivity.

Means for Attaining the Object

The present inventors have conducted concentrated studies in order to attain the above object. As a result, they discovered that the xylose-metabolizing ability of a yeast strain could be improved to a significant extent by bringing the yeast strain having xylose-metabolizing ability into contact with an acetic-acid-containing solution. This has led to the completion of the present invention.

The present invention includes the following.

(1) A method for producing ethanol comprising steps of: soaking a yeast strain having xylose-metabolizing ability in an acetic-acid-containing solution; and then, culturing the yeast strain in a xylose-containing medium to perform ethanol fermentation.

(2) The method for producing ethanol according to (1), wherein the yeast strain is a recombinant yeast strain into which a gene(s) involved in xylose metabolism is introduced.

(3) The method for producing ethanol according to (2), wherein the genes involved in xylose metabolism are the xylose reductase gene, the xylitol dehydrogenase gene, and the xylulokinase gene.

(4) The method for producing ethanol according to (1), wherein the yeast strain is soaked in an acetic-acid-containing solution under aerobic conditions.

(5) The method for producing ethanol according to (1), wherein the acetic-acid-containing solution is a mixture of a medium for yeast culture and acetic acid.

Effects of the Invention

According to the method for producing ethanol of the present invention, the xylose-metabolizing ability of a yeast strain having such ability can be improved, and ethanol productivity is consequently improved to a significant extent. According to the method for producing ethanol of the present invention, ethanol can be produced in a cost-effective manner with the use of, for example, a woody biomass.

EMBODIMENTS FOR CARRYING OUT THE INVENTION

Figure 1:
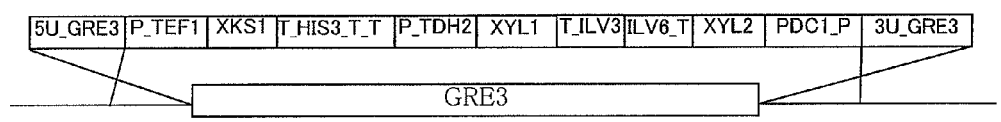
FIG. 1 schematically shows recombination implemented with the use of a DNA fragment intended for overexpression of the XYL1, XYL2, and XKS1 genes and disruption of the GRE3 gene.

Hereafter, the present invention is described in greater detail with reference to the drawings and the examples.

The method for producing ethanol of the present invention is a method for synthesizing ethanol from xylose contained in a medium with the use of a recombinant yeast strain having xylose-metabolizing ability. The method comprises a step of bringing the recombinant yeast strain into contact with an acetic-acid-containing solution. As a result of such step, the xylose-metabolizing ability of a recombinant yeast strain is improved to a significant extent, and ethanol productivity is consequently improved to a significant extent.

<Recombinant Yeast Strain>

A recombinant yeast strain used in the method for producing ethanol of the present invention comprises at least a gene(s) involved in xylose metabolism that has been introduced into the yeast strain's genome. Such recombinant yeast strain is capable of assimilating xylose contained in a medium and producing ethanol. Xylose contained in a medium may be obtained by saccharification of xylan or hemicellulose comprising xylose as a constituent sugar. Alternatively, it may be a substance supplied to a medium as a result of saccharification of xylan or hemicellulose contained in a medium by a carbohydrase (diastatic enzyme). In the case of the latter, the term "xylose contained in a medium" refers to the so-called simultaneous saccharification and fermentation process.

The term "gene involved in xylose metabolism" refers to a xylose reductase gene encoding the xylose reductase that converts xylose into xylitol, the xylitol dehydrogenase gene encoding the xylitol dehydrogenase that converts xylitol into xylulose, or the xylulokinase gene encoding xylulokinase that phosphorylates xylulose to produce xylulose 5-phosphate. Xylulose 5-phosphate produced by xylulokinase is metabolized through the pentose phosphate pathway.

A gene involved in xylose metabolism to be introduced into the yeast genome is not particularly limited, and examples thereof include the xylose reductase gene and the xylitol dehydrogenase gene derived from *Pichia stipitis* and the xylulokinase gene derived from *Saccharomyces cerevisiae* (see Eliasson, A. et al., Appl. Environ. Microbiol., 66: 3381-3386; and Toivari, M. N. et al., Metab. Eng., 3: 236-249). In addition, the xylose reductase gene derived from *Candida tropicalis* or *Candida prapsilosis* can also be used as the xylose reductase gene. The xylitol dehydrogenase gene derived from *Candida tropicalis* or *Candida prapsilosis* can be used as the xylitol dehydrogenase gene. The xylulokinase gene derived from *Pichia stipitis* can be used as the xylulokinase gene. The xylose isomerase gene derived from the *Streptomyces murinus* cluster can also be used.

A recombinant yeast strain used in the method for producing ethanol of the present invention may comprise a gene involved in sugar metabolism of glucose introduced therein, in addition to the gene involved in xylose metabolism mentioned above. For example, a recombinant yeast strain preferably has β-glucosidase activity resulting from the introduction of the β-glucosidase gene.

The term "β-glucosidase activity" used herein refers to an activity of catalyzing a hydrolysis reaction of a β-glycoside bond of a sugar. Specifically, β-glucosidase is capable of degrading a cellooligosaccharide, such as cellobiose, into glucose. It is preferable that the β-glucosidase gene be introduced in the form of a cell-surface display gene. The term "cell-surface display gene" used herein refers to a gene that is modified to display a protein to be encoded by the gene on a cell surface. For example, a cell-surface display β-glucosidase gene is a gene resulting from fusion of the β-glucosidase gene with a cell-surface localized protein gene. A cell-surface localized protein is fixed and present on a yeast cell surface layer. Examples include agglutinative proteins, such as α- or a-agglutinin and FLO proteins. In general, a cell-surface localized protein comprises an N-terminal secretory signal sequence and a C-terminal GPI anchor attachment recognition signal. While a cell-surface localized protein shares properties with a secretory protein in terms of the presence of a secretory signal, it differs from a secretory signal in that the cell-surface localized protein is transported while fixed to a cell membrane through a GPI anchor. When a cell-surface localized protein passes through a cell membrane, a GPI anchor attachment recognition signal sequence is selectively cut, it binds to a GPI anchor at a newly protruded C-terminal region, and it is then fixed to the cell membrane. Thereafter, the root of the GPI anchor is cut by phosphatidylinositol-dependent phospholipase C (PI-PLC). Subsequently, a protein separated from the cell membrane is integrated into a cell wall, fixed onto a cell surface layer, and then localized on a cell surface layer (see, for example, JP Patent Publication (Kokai) No. 2006-174767 A).

The β-glucosidase gene is not particularly limited, and an example is the β-glucosidase gene derived from *Aspergillus aculeatus* (Murai, et al., Appl. Environ. Microbiol., 64: 4857-4861). In addition, the β-glucosidase gene derived from *Aspergillus oryzae*, the β-glucosidase gene derived from *Clostridium cellulovorans*, and the β-glucosidase gene derived from *Saccharomycopsis fibligera* can be used.

<Production of Recombinant Yeast Strain>

The gene(s) involved in xylose metabolism mentioned above is/are introduced into a host yeast genome, and a recombinant yeast strain that can be used in the present invention can be produced. Examples of host yeast strains that can be used include, but are not particularly limited to, *Candida Shehatae*, *Pichia stipitis*, *Pachysolen tannophilus*, *Saccharomyces cerevisiae*, and *Schizosaccaromyces pombe*, with *Saccharomyces cerevisiae* being particularly preferable. Experimental yeast strains used from the viewpoint of experimental convenience or industrial (practical) strains used from the viewpoint of practical usefulness may also be used. Examples of industrial strains include yeast strains used for the production of wine, sake, and Shochu.

Use of a host yeast strain having homothallic properties is preferable. According to the technique disclosed in JP Patent Publication (Kokai) No. 2009-34036 A, the multiple copies of a gene can be easily introduced into the genome with the use of a yeast strain having homothallic properties. The term "yeast strain having homothallic properties" is the same as the term "homothallic yeast strain." Yeast strains having homothallic properties are not particularly limited, and any yeast strains can be used. An example of a yeast strain having homothallic properties is the *Saccharomyces cerevisiae* OC-2 train (NBRC2260), but yeast strains are not limited thereto. Examples of other yeast strains having homothallic properties include an alcohol-producing yeast (Taiken No. 396, NBRC0216) (reference: "*Alcohol kobo no shotokusei* (Various properties of alcohol-producing yeast)," *Shuken Kaiho*, No. 37, pp. 18-22, 1998.8), an ethanol-producing yeast isolated in Brazil and in Japan (reference: "*Brazil to Okinawa de bunri shita Saccharomyces cerevisiae yaseikabu no idengakuteki seishitsu* (Genetic properties of wild-type *Saccharomyces cerevisiae* isolated in Brazil and in Okinawa)," the Journal of the Japan Society for Bioscience, Biotechnology, and Agrochemistry, Vol. 65, No. 4, pp. 759-762, 1991.4), and 180 (reference: "*Alcohol Hakkoryoku no tsuyoi kobo no screening* (Screening of yeast having potent alcohol-fermenting ability)," the Journal of the Brewing Society of Japan, Vol. 82, No. 6, pp. 439-443, 1987.6). In addition, the HO gene may be introduced into a yeast strain exhibiting heterothallic phenotypes in an expressible manner, and the resulting strain can be used as a yeast strain having homothallic properties. That is, the term "yeast strain having homothallic properties" used herein also refers to a yeast strain into which the HO gene has been introduced in an expressible manner.

The *Saccharomyces cerevisiae* OC-2 strain is particularly preferable since it has heretofore been used for wine brewing, and the safety thereof has been verified. As described in the examples below, the *Saccharomyces cerevisiae* OC-2 strain is preferable in terms of its excellent promoter activity at high sugar concentration. In particular, the *Saccharomyces cerevisiae* OC-2 strain is preferable in terms of its excellent promoter activity for the pyruvate decarboxylase gene (PDC1) at high sugar concentrations.

Promoters of genes to be introduced are not particularly limited. For example, promoters of the glyceraldehyde-3-phosphate dehydrogenase gene (TDH3), the 3-phosphoglycerate kinase gene (PGK1), and the high-osmotic pressure response 7 gene (HOR7) can be used. The promoter of the pyruvate decarboxylase gene (PDC1) is particularly preferable in terms of its high capacity for expressing target genes in a downstream region at high levels.

Specifically, such gene may be introduced into the yeast genome together with an expression-regulating promoter or another expression-regulated region. Such gene may be introduced into a host yeast genome in such a manner that expression thereof is regulated by a promoter or another expression-regulated region of a gene that is inherently present therein.

The gene can be introduced into the genome by any conventional technique known as a yeast transformation technique. Specific examples include, but are not limited to, electroporation (Meth. Enzym., 194, p. 182, 1990), the spheroplast technique (Proc. Natl. Acad. Sci., U.S.A., 75, p. 1929, 1978), and the lithium acetate method (J. Bacteriology, 153, p. 163, 1983; Proc. Natl. Acad. Sci., U.S.A., 75, p. 1929, 1978; Methods in yeast genetics, 2000 Edition: A Cold Spring Harbor Laboratory Course Manual).

<Production of Ethanol>

When producing ethanol with the use of the recombinant yeast strain described above, the recombinant yeast strain is brought into contact with an acetic-acid-containing solution before conducting ethanol fermentation by culture in a xylose-containing medium. An acetic-acid-containing solution may be either an aqueous solution of acetic acid or a liquid medium containing acetic acid. An aqueous solution of acetic acid is obtained by dissolving acetic acid in water. A liquid medium containing acetic acid can be prepared by adding acetic acid to a medium for yeast culture such as SD medium, YPD medium, YPAD medium, or YM medium. The concentration of acetic acid contained in an acetic-acid-containing solution is not particularly limited. For example, it is 1 to 20 g/l, preferably 2 to 10 g/l, and more preferably 3 to 5 g/l. When the concentration of acetic acid contained in an acetic-acid-containing solution is lower than the lower limit of the above range, the xylose-metabolizing ability of the recombinant yeast strain may not be improved to a significant extent. When the concentration of acetic acid contained in an acetic-acid-containing solution is higher than the upper limit of the above range, growth of the recombinant yeast strain may be inhibited.

The duration during which the recombinant yeast strain remains in contact with an acetic-acid-containing solution is not particularly limited. For example, such duration is at least 1 hour, preferably at least 3 hours, and more preferably at least 10 hours. When such duration is shorter than the aforementioned duration, the xylose-metabolizing ability of the recombinant yeast strain may not improve to a significant extent.

The recombinant yeast strain may be brought into contact with an acetic-acid-containing solution by introducing the recombinant yeast strain into an acetic-acid-containing solution and subjecting the solution to stirring or shaking. When the recombinant yeast strain is brought into contact with an acetic-acid-containing solution, the temperature of the solution is, for example, 20° C. to 40° C., preferably 25° C. to 37° C., and more preferably 28° C. to 35° C.

It is particularly preferable that the recombinant yeast strain be brought into contact with an acetic-acid-containing solution with the use of a liquid medium containing acetic acid as an acetic-acid-containing solution under aerobic conditions. Since the recombinant yeast strain is brought into contact with an acetic-acid-containing solution, the xylose-metabolizing ability can be improved, and the amount of cells necessary for ethanol fermentation can be acquired through cell growth.

After the recombinant yeast strain is brought into contact with an acetic-acid-containing solution, the recombinant yeast strain is recovered from the acetic-acid-containing solution, and ethanol fermentation is carried out in a xylose-containing medium. The recombinant yeast strain can be recovered from the acetic-acid-containing solution by any means without particular limitation. For example, techniques such as centrifugation or filtration may be employed. When recovering the recombinant yeast strain from the acetic-acid-containing solution, it is preferable that as much of the acetic-acid-containing solution be removed as possible, so as to prevent inhibition of the growth of the recombinant yeast strain and inhibition of the ethanol production using the recombinant yeast strain caused by carry-over of the acetic-acid-containing solution in the xylose-containing medium used for ethanol fermentation. In other words, a certain amount of the acetic-acid-containing solution may carry over in the xylose-containing medium, provided that the degrees of inhibition of the growth of the recombinant yeast strain and inhibition of the ethanol production using the recombinant yeast strain are insignificant, and provided that such degrees are acceptable from the viewpoint of the efficiency of ethanol production. After the recombinant yeast strain is recovered from the acetic-acid-containing solution, the recombinant yeast strain may be subjected to washing in order to remove the acetic-acid-containing solution.

A xylose-containing medium used for ethanol fermentation may contain at least xylose as a carbon source, and such medium may contain another carbon source such as glucose. A medium used for ethanol fermentation may be prepared by adding a saccharified solution resulting from saccharification of a cellulose-based biomass to a basal medium. In such a case, a saccharified solution contains xylose derived from hemicellulose contained in a cellulosic biomass.

A medium used for ethanol fermentation may contain a cellulose-based biomass. In this case, the process of ethanol fermentation using the recombinant yeast strain is the so-called simultaneous saccharification and fermentation process. With the simultaneous saccharification and fermentation process, the step of saccharification of a cellulose-based biomass is carried out simultaneously with the process of ethanol fermentation. Prior to the simultaneous saccharification and fermentation process, a cellulose-based biomass may be subjected to a conventional pretreatment technique. Such pretreatment techniques are not particularly limited. For example, a lignin may be degraded by a microorganism, or a cellulose-based biomass may be ground.

The recombinant yeast strain is capable of assimilating xylose contained in a medium and producing ethanol in a medium of any type. Methods of saccharification are not particularly limited, and, for example, an enzymatic method involving the use of a cellulase preparation, such as cellulase or hemicellulase, may be employed. A cellulase preparation contains a plurality of enzymes involved in degradation of a cellulose chain and a hemicellulose chain, and it exhibits a plurality of types of activity, such as endoglucanase activity, endoxylanase activity, cellobiohydrolase activity, glucosidase activity, and xylosidase activity. Cellulase preparations are not particularly limited, and examples include cellulases produced by *Trichoderma reesei* and *Acremonium cellulolyticus*. A commercially available cellulase preparation may also be used.

According to the simultaneous saccharification and fermentation process, a cellulase preparation and the recombinant microorganism are added to a medium containing a cellulose-based biomass (a biomass after pretreatment may be used), and the recombinant yeast strain is cultured at a given temperature. Culture may be carried out at any temperature without particular limitation, and the temperature may be 25° C. to 45° C., and preferably 30° C. to 40° C. from the viewpoint of ethanol fermentation efficiency. The pH level of the culture solution is preferably 4 to 6. When conducting culture, stirring or shaking may be carried out.

According to the method for producing ethanol with the use of the recombinant yeast strain of the present invention, ethanol fermentation is followed by recovery of ethanol from the medium. Ethanol may be recovered by any conventional means without particular limitation. After the completion of the process of ethanol fermentation mentioned above, for example, a liquid layer containing ethanol is separated from a solid layer containing the recombinant yeast strain or solid matter via solid-solution separation. Thereafter, ethanol contained in a liquid layer is separated and purified by distillation, so that highly purified ethanol can be recovered. The degree of ethanol purification can be adequately determined in accordance with the purpose of use of the ethanol.

EXAMPLES

Hereafter, the present invention is described in greater detail with reference to the examples, although the technical scope of the present invention is not limited to these examples.

Example 1

In this example, a copy of a GRE3 gene of a diploid yeast strain (OC2-T, Saitoh, S. et al., J. Ferment. Bioeng., 1996, vol. 81, pp. 98-103) was disrupted and the XYL1, XYL2, and XKS1 genes were introduced thereinto, so as to produce a xylose-assimilating yeast strain.

Production of DNA Fragment Intended for Overexpression of XYL1, XYL2, and XKS1 Genes and Disruption of GRE3 Gene A DNA fragment containing the GRE3 gene and its 5' upstream and 3' downstream untranslated regions was amplified by PCR using the genomic DNA of the BY4742 yeast strain (Open Biosystems) as a template. A pair of PCR primers TB2358 (5'-TGGGAATATTACCGCTCGAAG-3': SEQ ID NO: 1) and TB2359 (5'-AAGGGGGAAGGTGTG-GAATC-3': SEQ ID NO: 2) was used. PCR primers used for amplification of the DNA sequence of the BY4742 yeast strain were designed with reference to the DNA sequence data stored in the *Saccharomyces Genome* Database. With the use of the pUC19 plasmid as a template, a linear DNA fragment containing full-length pUC19 that seemed to have been cleaved at the pUC19 multicloning site was amplified by PCR. A pair of PCR primers TB2373 (5'-CACACCTTC-CCCCTTGATCCTCTAGAGTCGACC-3': SEQ ID NO: 3) and TB2374 (5'-GCGGTAATATTCCCAGATCCCCGGG-TACCGAGCTC-3': SEQ ID NO: 4) was used. The two above DNA fragments were subjected to cloning using the In-Fusion™ Advantage PCR Cloning Kit (Takara Bio), and the resultant was designated as pUC19-5U_GRE3-GRE3-3U_GRE3.

With the use of pUC19-5U_GRE3-GRE3-3U_GRE3 as a template, the DNA fragment containing the GRE3 gene, its 5' upstream and 3' downstream untranslated regions, and pUC19 was amplified by PCR. With the use of the genomic DNA of the BY4742 yeast strain as a template, the DNA fragment containing the TEF1 promoter region and the DNA fragment containing the XKS1 gene and the HIS3 terminator region were amplified by PCR. A pair of PCR primers TB3018 (5'-AACGAGGCGCGCTCTTCCAGCCAG-TAAAATCCA-3': SEQ ID NO: 5) and TB3017 (5'-GC-TATGGTGTGTGGGCTTTAAAAAATTTC-CAATTTTCCTTTACG-3': SEQ ID NO: 6), that of TB2210 (5'-CCCACACACCATAGCTTCAAAATG-3': SEQ ID NO: 7) and TB2269 (5'-TCTTTAGATTAGATTGCTAT-GCTTTCTTTCTAATGAGCAAG-3': SEQ ID NO: 8), that of TB2345 (5'-AATCTAATCTAAAGAATGTTGTGT-TCAGTAATTCAGAGAC-3': SEQ ID NO: 9) and TB2346 (5'-CTGCGGCCGGCCGCATTAGAT-GAGAGTCTTTTCCAGTTC-3': SEQ ID NO: 10), and that of TB1401 (5'-TGCGGCCGGCCGCAGC-3': SEQ ID NO: 11) and TB2683 (5'-GCGCCTCGTTCAGAATGA-3': SEQ ID NO: 12) were used, respectively. The four above DNA fragments were subjected to cloning using the In-Fusion™ Advantage PCR Cloning Kit, and the resultant was designated as pUC19-5U_GRE3-P_TEF1-XKS1-T_HIS3-3U_GRE3.

With the use of pUC19-5U_GRE3-P_TEF1-XKS1-T_HIS3-3U_GRE3 as a template, a linear DNA fragment containing a full-length plasmid that seemed to have been cleaved between the HIS3 terminator region and the 3' downstream untranslated region of the GRE3 gene was amplified by PCR. With the use of the genomic DNA of the BY4742 yeast strain as a template, a DNA fragment containing the TDH2 promoter region and a DNA fragment containing the ILV3 terminator region were amplified by PCR. With the use of the genomic DNA of *Pichia stipitis* as a template, the XYL1 gene was amplified by PCR. A pair of PCR primers TB9020 (5'-TCCAGCCAGTAAAATCCATAC-3': SEQ ID NO: 13) and TB2457 (5'-CCGTCAAGAGAGCGCGC-CTCGTTCAG-3': SEQ ID NO: 14), that of TB2844 (5'-GCGCTCTCTTGACGGGTATTCTGAGCATCTTAC-3': SEQ ID NO: 15) and TB2595 (5'-TTTGTTTTGTTTGTTTGTGTGATGAATTTAATTTG-3': SEQ ID NO: 16), that of TB2314 (5'-AACAAACAAAA-CAAAATGCCTTCTATTAAGTTGAAC-3': SEQ ID NO: 17) and TB2455 (5'-GGGGCCTATAATGCATTAGAC-GAAGATAGGAATCTTG-3': SEQ ID NO: 18), and that of TB2456 (5'-AACAAACAAAACAAAATGCCTTCTAT-TAAGTTGAAC-3': SEQ ID NO: 19) and TB3019 (5'-ATTT-TACTGGCTGGAATTTCGTAGATTATAAT-
TAAGGCGAC-3': SEQ ID NO: 20) were used, respectively. PCR primers used for amplification of the XYL1 gene sequence were designed with reference to the XYL1 gene of *Pichia stipitis* registered with GeneBank (Accession Number: XM_001385144). The four above DNA fragments were subjected to cloning using the In-Fusion™ Advantage PCR Cloning Kit, and the resultant was designated as pUC19-5U_GRE3-P_TEF1-XKS1-T_HIS3-P_TDH2-XYL1-T_ILV3-3U_GRE3.

With the use of pUC19-5U_GRE3-P_TEF1-XKS1-T_HIS3-P_TDH2-XYL1-T_ILV3-3U_GRE3 as a template, a linear DNA fragment containing a full-length plasmid that seemed to have been cleaved between the ILV3 terminator region and the 3' downstream untranslated region of the GRE3 gene was amplified by PCR. With the use of the genomic DNA of the BY4742 yeast strain as a template, a DNA fragment containing the PDC1 promoter region and a DNA fragment containing the ILV6 terminator region were amplified by PCR. With the use of the genomic DNA of *Pichia stipitis* as a template, the XYL2 gene was amplified by PCR. A pair of PCR primers TB2375 (5'-AGTTGCTTGA-CACGGTGGAAGAAGGTCCAGCCAGTAAAATCCATA-3': SEQ ID NO: 21) and TB3021 (5'-ATTTCGTAGAT-TATAATTAAGGCGAC-3': SEQ ID NO: 22), that of TB2010 (5'-TTTGATTGATTTGACTGTGTTATTTTGC-3': SEQ ID NO: 23) and TB2261 (5'-CCGTGTCAAGCAACTATGGG-3': SEQ ID NO: 24), that of TB3022 (5'-TATAATCTAC-GAAATTAATAAGAAAGGTGACCGTG-3': SEQ ID NO: 25) and TB2347 (5'-GTTAGTCTCTCGGCCTTGCG-3': SEQ ID NO: 26), and that of TB2351 (5'-GGCCGAGAGAC-TAACTTACTCAGGGCCGTCAAT-3': SEQ ID NO: 27) and TB2352 (5'-GTCAAATCAATCAAAATGACTGCTAAC-CCTTCC-3': SEQ ID NO: 28) were used, respectively. PCR primers used for amplification of the XYL2 gene sequence were designed with reference to the XYL2 gene of *Pichia stipitis* registered with GeneBank (Accession Number: AF127801 or X55392). The four above DNA fragments were subjected to cloning using the In-Fusion™ Advantage PCR Cloning Kit, and the resultant was designated as pUC19-5U_GRE3-P_TEF1-XKS1-T_HIS3-P_TDH2-XYL1-T_ILV3-ILV6_T-XYL2-PDC1_P-3U_GRE3.

With the use of pUC19-5U_GRE3-P_TEF1-XKS1-T_HIS3-P_TDH2-XYL1-T_ILV3-ILV6_T-XYL2-PDC1_P-3U_GRE3 as a template, a DNA fragment comprising a region from the 5' upstream untranslated region of the GRE3 gene to the 3' downstream untranslated region of the GRE3 gene was amplified by PCR. The resulting fragment (FIG. 1) was used for preparation of a strain intended for overexpression of the XYL1, XYL2, and XKS1 genes and disruption of the GRE3 gene.

Preparation of Strain Overexpressing XYL1, XYL2, and XKS1 Genes and Hetero-Disrupting GRE3 Gene With the use of the DNA fragment intended for overexpression of the XYL1, XYL2, and XKS1 genes and disruption of the GRE3 gene, the OC2-T strain was transformed using the Frozen-EZ Yeast Transformation II kit (ZYMO RESEARCH) in accordance with the protocols included in the kit. Thereafter, the strain was inoculated on a plate using xylose as a single carbon source and then cultured at 30° C. for 7 days to obtain a transformant. Genomic DNA was prepared from the transformant, PCR was carried out using primers located at the outside of the inserted DNA fragment and at the inside of the vector; i.e., TB2356 (5'-TGGGGCTAAAC-GAGATTTGG-3': SEQ ID NO: 29) and TB592 (5'-GAAATTTAGTATGCTGTGCTTGGG-3': SEQ ID NO: 30), so as to confirm that a copy of the DNA of interest had been normally incorporated into the chromosome.

Fermentation Test

The transformant was inoculated into YPD medium (10 g/l yeast extract, 20 g/l peptone, and 20 g/l glucose) or YPD medium containing acetic acid (10 g/l yeast extract, 20 g/l peptone, 20 g/l glucose, and 1 to 5 g/l acetic acid; adjusted at pH 5 with ammonia), and shake culture was conducted at 30° C. for 24 hours. After the completion of culture, cells were recovered by centrifugation at 2,000 g for 3 minutes.

A xylose medium (60 g/l xylose and 10 g/l yeast extract), a glucose/xylose medium (90 g/l glucose, 60 g/l xylose, and 10 g/l yeast extract), or a glucose medium (90 g/l glucose and 10 g/l yeast extract) (50 ml) was introduced into a 50-ml flask, cells were inoculated to a density of 0.3 g/l on a dry basis, fermentation was conducted at 80 rpm (shake width: 35 mm) at 34° C. for 48 hours, and concentrations of ethanol and xylose were measured by HPLC (LC-10A, Shimadzu Seisakusho). Measurement was conducted using the Aminex-HPX-87H column (BioRad) and the differential refractometer (RID-10A, Shimadzu Seisakusho), and analysis was conducted using a mobile phase of 0.01 N $H_2SO_4$ at a flow rate of 0.6 ml/min at 30° C.

Figure 2:
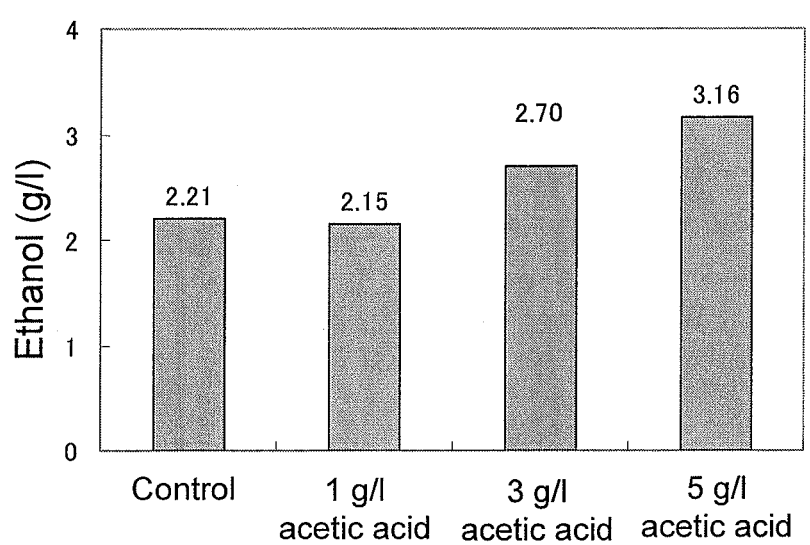
FIG. 2 is a characteristic diagram showing the results of analyzing ethanol concentration after the fermentation test.

FIG. 2 shows the results of analysis of ethanol concentration. As shown in FIG. 2, in case of the xylose medium, the speed of ethanol production was found to be improved in a sample cultured in the medium containing 3 g/l or more acetic acid, compared with a sample cultured in the medium containing no acetic acid, as a result of the fermentation test. In contrast, no difference was observed in the speed of ethanol production in case of the glucose medium.

Figure 3:
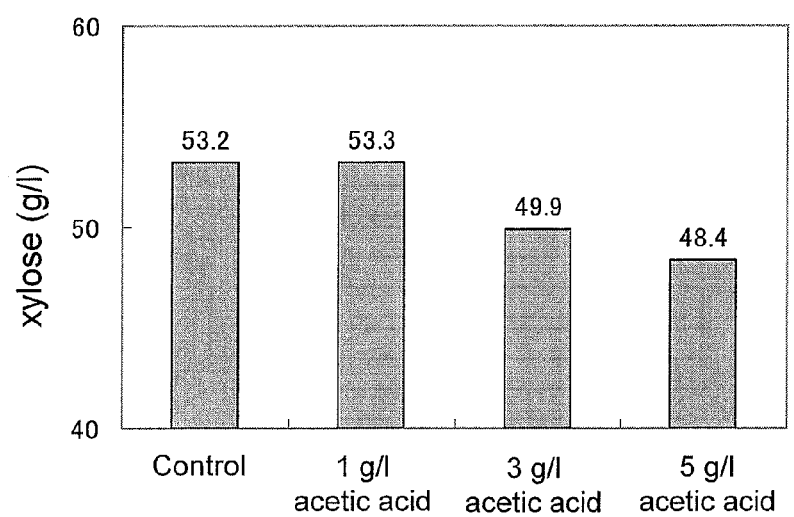
FIG. 3 is a characteristic diagram showing the results of analyzing xylose concentration after the fermentation test.

FIG. 3 shows the results of analysis of xylose concentration. As shown in FIG. 3, in case of the glucose/xylose medium, the speed of xylose consumption was improved in a sample cultured in the medium containing 3 g/l or more acetic acid. However, no difference was observed between the sample and the control sample in terms of the amount of glucose consumed.

By bringing the recombinant yeast strain having xylose-metabolizing ability into contact with an acetic-acid-containing solution (a liquid medium containing acetic acid in this example) prior to the step of ethanol fermentation, the xylose-metabolizing ability of the recombinant yeast strain was found to have been improved to a significant extent based on the results attained above. When the recombinant yeast strain having xylose-metabolizing ability was brought into contact with an acetic-acid-containing solution, the glucose-metabolizing ability of the recombinant yeast strain was not improved to a significant extent. This demonstrates that, when the recombinant yeast strain having xylose-metabolizing ability is brought into contact with the acetic-acid-containing solution, xylose-metabolizing ability of the recombinant yeast strain among various types of ability for carbon source assimilation can be specifically improved.

The invention claimed is:

1. A method for producing ethanol comprising steps of: bringing a recombinant yeast strain having xylose-metabolizing ability into contact with an acetic-acid-containing solution under aerobic conditions, recovering the recombinant yeast from the acetic-acid-containing solution, and then, culturing the yeast strain in a xylose-containing medium to perform ethanol fermentation.

2. The method for producing ethanol according to claim 1, wherein the recombinant yeast comprises a nucleic acid encoding a xylose reductase, a nucleic acid encoding a xylitol dehydrogenase, and a nucleic acid encoding a xylulokinase.

3. The method for producing ethanol according to claim 1, wherein the acetic-acid-containing solution is a mixture of a medium for yeast culture and acetic acid.

* * * * *

SEQUENCE LISTING

```
<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA

<400> SEQUENCE: 1
tgggaatatt accgctcgaa g                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
aagggggaag gtgtggaatc                                                20
```

```
<210> SEQ ID NO 3
<211> LENGTH: 33
<212> TYPE: DNA
<213> ORGANISM: Artificial Sequence
<220> FEATURE:
<223> OTHER INFORMATION: Synthetic DNA

<400> SEQUENCE: 3
cacaccttcc cccttgatcc tctagagtcg acc                              33

<210> SEQ ID NO 4
<211> LENGTH: 35
<212> TYPE: DNA
<213> ORGANISM: Artificial Sequence
<220> FEATURE:
<223> OTHER INFORMATION: Synthetic DNA

<400> SEQUENCE: 4
gcggtaatat tcccagatcc ccgggtaccg agctc                            35

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA

<400> SEQUENCE: 5
aacgaggcgc gctcttccag ccagtaaaat cca                              33

<210> SEQ ID NO 6
<211> LENGTH: 44
<212> TYPE: DNA
<213> ORGANISM: Artificial Sequence
<220> FEATURE:
<223> OTHER INFORMATION: Synthetic DNA

<400> SEQUENCE: 6
gctatggtgt gtgggcttta aaaatttcc aattttcctt tacg                  44

<210> SEQ ID NO 7
<211> LENGTH: 24
<212> TYPE: DNA
<213> ORGANISM: Artificial Sequence
<220> FEATURE:
<223> OTHER INFORMATION: Synthetic DNA

<400> SEQUENCE: 7
cccacacacc atagcttcaa aatg                                        24

<210> SEQ ID NO 8
<211> LENGTH: 41
<212> TYPE: DNA
<213> ORGANISM: Artificial Sequence
<220> FEATURE:
<223> OTHER INFORMATION: Synthetic DNA

<400> SEQUENCE: 8
tctttagatt agattgctat gctttctttc taatgagcaa g                     41

<210> SEQ ID NO 9
<211> LENGTH: 40
<212> TYPE: DNA
<213> ORGANISM: Artificial Sequence
<220> FEATURE:
<223> OTHER INFORMATION: Synthetic DNA
```

<400> SEQUENCE: 9
aatctaatct aaagaatgtt gtgttcagta attcagagac                            40

<210> SEQ ID NO 10
<211> LENGTH: 39
<212> TYPE: DNA
<213> ORGANISM: Artificial Sequence
<220> FEATURE:
<223> OTHER INFORMATION: Synthetic DNA

<400> SEQUENCE: 10
ctgcggccgg ccgcattaga tgagagtctt ttccagttc                             39

<210> SEQ ID NO 11
<211> LENGTH: 16
<212> TYPE: DNA
<213> ORGANISM: Artificial Sequence
<220> FEATURE:
<223> OTHER INFORMATION: Synthetic DNA

<400> SEQUENCE: 11
tgcggccggc cgcagc                                                      16

<210> SEQ ID NO 12
<211> LENGTH: 18
<212> TYPE: DNA
<213> ORGANISM: Artificial Sequence
<220> FEATURE:
<223> OTHER INFORMATION: Synthetic DNA

<400> SEQUENCE: 12
gcgcctcgtt cagaatga                                                    18

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA

<400> SEQUENCE: 13
tccagccagt aaaatccata c                                                21

<210> SEQ ID NO 14
<211> LENGTH: 26
<212> TYPE: DNA
<213> ORGANISM: Artificial Sequence
<220> FEATURE:
<223> OTHER INFORMATION: Synthetic DNA

<400> SEQUENCE: 14
ccgtcaagag agcgcgcctc gttcag                                           26

<210> SEQ ID NO 15
<211> LENGTH: 33
<212> TYPE: DNA
<213> ORGANISM: Artificial Sequence
<220> FEATURE:
<223> OTHER INFORMATION: Synthetic DNA

<400> SEQUENCE: 15
gcgctctctt gacgggtatt ctgagcatct tac                                   33

<210> SEQ ID NO 16
<211> LENGTH: 35

<210> SEQ ID NO 16
<211> LENGTH: 35
<212> TYPE: DNA
<213> ORGANISM: Artificial Sequence
<220> FEATURE:
<223> OTHER INFORMATION: Synthetic DNA

<400> SEQUENCE: 16
tttgttttgt ttgtttgtgt gatgaattta atttg    35

<210> SEQ ID NO 17
<211> LENGTH: 36
<212> TYPE: DNA
<213> ORGANISM: Artificial Sequence
<220> FEATURE:
<223> OTHER INFORMATION: Synthetic DNA

<400> SEQUENCE: 17
aacaaacaaa acaaaatgcc ttctattaag ttgaac    36

<210> SEQ ID NO 18
<211> LENGTH: 37
<212> TYPE: DNA
<213> ORGANISM: Artificial Sequence
<220> FEATURE:
<223> OTHER INFORMATION: Synthetic DNA

<400> SEQUENCE: 18
ggggcctata atgcattaga cgaagatagg aatcttg    37

<210> SEQ ID NO 19
<211> LENGTH: 36
<212> TYPE: DNA
<213> ORGANISM: Artificial Sequence
<220> FEATURE:
<223> OTHER INFORMATION: Synthetic DNA

<400> SEQUENCE: 19
aacaaacaaa acaaaatgcc ttctattaag ttgaac    36

<210> SEQ ID NO 20
<211> LENGTH: 41
<212> TYPE: DNA
<213> ORGANISM: Artificial Sequence
<220> FEATURE:
<223> OTHER INFORMATION: Synthetic DNA

<400> SEQUENCE: 20
attttactgg ctggaatttc gtagattata attaaggcga c    41

<210> SEQ ID NO 21
<211> LENGTH: 45
<212> TYPE: DNA
<213> ORGANISM: Artificial Sequence
<220> FEATURE:
<223> OTHER INFORMATION: Synthetic DNA

<400> SEQUENCE: 21
agttgcttga cacggtggaa gaaggtccag ccagtaaaat ccata    45

<210> SEQ ID NO 22
<211> LENGTH: 26
<212> TYPE: DNA
<213> ORGANISM: Artificial Sequence
<220> FEATURE:
<223> OTHER INFORMATION: Synthetic DNA

<400> SEQUENCE: 22

```
atttcgtaga ttataattaa ggcgac                                      26

<210> SEQ ID NO 23
<211> LENGTH: 28
<212> TYPE: DNA
<213> ORGANISM: Artificial Sequence
<220> FEATURE:
<223> OTHER INFORMATION: Synthetic DNA

<400> SEQUENCE: 23
tttgattgat ttgactgtgt tattttgc                                    28

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA

<400> SEQUENCE: 24
ccgtgtcaag caactatggg                                             20

<210> SEQ ID NO 25
<211> LENGTH: 35
<212> TYPE: DNA
<213> ORGANISM: Artificial Sequence
<220> FEATURE:
<223> OTHER INFORMATION: Synthetic DNA

<400> SEQUENCE: 25
tataatctac gaaattaata agaaaggtga ccgtg                            35

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
gttagtctct cggccttgcg                                             20

<210> SEQ ID NO 27
<211> LENGTH: 33
<212> TYPE: DNA
<213> ORGANISM: Artificial Sequence
<220> FEATURE:
<223> OTHER INFORMATION: Synthetic DNA

<400> SEQUENCE: 27
ggccgagaga ctaacttact cagggccgtc aat                              33

<210> SEQ ID NO 28
<211> LENGTH: 33
<212> TYPE: DNA
<213> ORGANISM: Artificial Sequence
<220> FEATURE:
<223> OTHER INFORMATION: Synthetic DNA

<400> SEQUENCE: 28
gtcaaatcaa tcaaaatgac tgctaaccct tcc                              33

<210> SEQ ID NO 29
<211> LENGTH: 20
<212> TYPE: DNA
<213> ORGANISM: Artificial Sequence
```

```
<220> FEATURE:
<223> OTHER INFORMATION: Synthetic DNA

<400> SEQUENCE: 29
tggggctaaa cgagatttgg                                               20

<210> SEQ ID NO 30
<211> LENGTH: 24
<212> TYPE: DNA
<213> ORGANISM: Artificial Sequence
<220> FEATURE:
<223> OTHER INFORMATION: Synthetic DNA

<400> SEQUENCE: 30
gaaatttagt atgctgtgct tggg                                          24
```